United States Patent [19]

Schmor et al.

[11] Patent Number: 5,282,235
[45] Date of Patent: Jan. 25, 1994

[54] NITROGEN DETECTOR AND METHOD OF DETECTING

[76] Inventors: Paul W. Schmor, 11558 Pemberton Crescent, Delta, British Columbia, Canada, V4C 3J4; Lothar R. Buchmann, 3700 Springfield Drive, Richmond, British Columbia, Canada, V7E 1Z4; Joel G. Rogers, 2460 West 12th Avenue, Vancouver, British Columbia, Canada, V6K 2P1

[21] Appl. No.: 5,281

[22] Filed: Jan. 19, 1993

[51] Int. Cl.$^5$ .................................. G01N 23/06
[52] U.S. Cl. ........................... 378/53; 378/57
[58] Field of Search ................................ 378/53, 57

[56] References Cited

U.S. PATENT DOCUMENTS

| | | | |
|---|---|---|---|
| 4,941,162 | 7/1990 | Vartsky et al. | 378/53 |
| 5,040,200 | 8/1991 | Ettinger et al. | 378/57 |
| 5,115,459 | 5/1992 | Bertozzi | 378/57 |
| 5,125,015 | 6/1992 | Shimoni et al. | 378/57 |

OTHER PUBLICATIONS

"Nuclear and X-Ray Technologies for Airport Security", Grodzins, MIT Symposium Apr. 17, 1990.

Primary Examiner—Craig E. Church
Attorney, Agent, or Firm—Griffin, Butler, Whisenhunt & Kurtossy

[57] ABSTRACT

An apparatus and method for determining the amount of nitrogen in an object. A support means is provided for supporting the object, and at least one gamma ray beam is disposed on one side of the support for producing a beam of about 9.2 MeV gamma rays and in sufficient intensity to cause measurable resonant absorption by $^{14}$N in the nitrogenous compounds. A directing device is disposed between the gamma ray beam and the support for directing the gamma ray beam to the support at a predetermined angle, such that the gamma ray beam forms a path which encounters at least a portion of the object when disposed on the support. An array of gamma ray detectors are disposed on an opposite side of the support for detecting gamma rays of about 9.2 MeV transmitted through the object at both resonant and non-resonant angles. A computation device computes the difference in the amount of transmitted gamma rays detected by the detectors at the resonant angles and non-resonant angles, and the difference is related to the amount of nitrogenous compounds in the object.

40 Claims, 2 Drawing Sheets

NITROGEN DETECTOR AND METHOD OF DETECTING

The present invention relates to an apparatus for detecting nitrogen in a substance and to a method of such detection. More specifically, the invention relates to such nitrogen detection for determining the presence or amount of nitrogen in an object containing nitrogenous compounds, as well as non-nitrogenous compounds.

BACKGROUND OF THE INVENTION

It is often important to determine the amount of nitrogen in an object containing nitrogenous compounds and non-nitrogenous compounds. Nitrogen is a common element of many important compounds. For example, nitrogen is a key element in proteins, certain plastics, fertilizers, explosives, certain medications, and even illegal drugs. The art has proposed detection of nitrogenous compounds by gamma ray scattering or absorption by the nitrogen of the compounds, and that scattering or absorption is detected and analyzed for determining the amount of nitrogen in an object of interest. Very briefly, in those techniques, the object of interest having nitrogenous compounds therein is placed in the path of a gamma ray beam. When the beam is of required characteristics, the gamma rays are resonantly absorbed or scattered by the nitrogen in the object being examined, and those gamma rays are detected by conventional detectors which provide output signals proportional to the amount of nitrogen in the object being examined. The details of the theory of such detection devices are well known, and a rather complete description of the theory is presented in U.S. Pat. Nos. 4,941,162 and 5,040,200, which patents are incorporated herein by reference and relied upon for the details of the theory and conventional apparatus for carrying out gamma ray detection of nitrogenous compounds.

However, there have been common difficulties in this prior art in that gamma ray scattering or absorption are subject to special limitations in connection with the manner in which the gamma ray beam is applied and in connection with suitable detectors for the transmitted gamma rays. A representative example of those difficulties is disclosed in U.S. Pat. No. 4,941,162. That patent is, specifically, directed to the detection of nitrogenous explosive material, e.g. explosive material concealed in a travel bag, e.g. luggage. In the arrangement of that patent, a gamma ray source emits gamma rays of a desired and monitored flux, and those gamma rays are limited in divergence by a collimator so that a beam of gamma rays will intersect luggage moving on a conveyor near the collimator. Explosive material (which will normally contain nitrogenous compounds) will cause gamma ray attenuation, indicating the presence of nitrogenous compounds in the luggage.

However, that arrangement has two very decided disadvantages. Firstly, in that arrangement, the attenuation of the gamma rays by nuclear resonance takes place with non-resonant attenuation. Accordingly, in order to determine the presence of or amount of nitrogenous compound, that arrangement requires two different sets of detectors, i.e. one set of detectors which can determine the resonant attenuation and one set of detectors which can determine the non-resonant attenuation. These two sets of detectors are linked to a data analysis system which then uses both the data from the resonant detectors and the non-resonant detectors to make a determination of the presence of nitrogenous compounds. This considerably complicates the detection of nitrogenous compounds and, as a result, considerably lessens the accuracy of that determination.

A further difficulty of that arrangement, which is common to the art, is that a result of that arrangement is the necessity to use nitrogen-rich detectors, which, according to the prior art, were required. This was thought to be required because nuclear resonant scattering requires resonant detectors to select the relevant energy portion of the transmitted flux spectrum which contains the resonance absorption information, and it was thought that nitrogen-rich detectors were required to achieve that function.

Further, and partly as a result of the foregoing, the accuracy of detection of nitrogenous compounds is not to the degree required, and to ensure that luggage does not contain nitrogenous explosives, it is necessary in that prior art arrangement to orient the luggage, with respect to the gamma ray beam, at various angles, as the luggage passes through that beam. This considerably complicates and slows the examination of luggage. For example, if the nitrogenous explosive material is in thin sheet form, and the luggage passes that beam with the thin sheet perpendicular to the beam, the lack of desired accuracy could easily not detect the presence of the nitrogenous explosive material in thin sheet form. Thus, it is necessary in that prior art arrangement to examine the luggage as it is passed through the beam a plurality of times, but at different angles to the beam.

While this lack of desired degree of accuracy of detection could be quite dangerous in regard to luggage to be boarded on an aircraft, that undesired degree of detection is also serious in other detections of nitrogenous compounds. For example, the same degree of detection provided by that arrangement could also fail to detect illegal drugs in a particular design of a container for the drugs. Somewhat similarly, for example, where the protein content of a flowing dairy product, such as milk, is to be detected, that degree of detection could give erroneous protein content results. Also similarly, where the protein content of a grain or cereal is to be detected, that degree of accuracy could also give erroneous results.

As can, therefore, be appreciated, it would be of substantial advantage in the art to provide apparatus and methods for gamma ray detection of nitrogenous compounds in an object also having non-nitrogenous compounds, where the accuracy of the detection is considerably increased. It would also be of substantial advantage to the art to provide such apparatus and methods where the apparatus and method are less complex and do not require separate determinations of resonant attenuation and non-resonant attenuation, with the attendant necessity of separate arrays of resonant detectors and non-resonant detectors.

BRIEF DESCRIPTION OF THE INVENTION

When about 1.75 MeV protons impinge on a suitable target, e.g. $^{13}C$, they have a high probability of resonantly producing about 9.2 MeV gamma rays. These gamma rays are emitted from the target at all angles, but not uniformly. It has been found that those gamma rays emitted at about 80.66°±about 0.5°, with respect to the direction of the proton beam, have a large probability of being resonantly absorbed by $^{14}N$. This particular angular range is determined by the kinematics of the reactions. The precise energy of the emitted gamma rays depends (in view of the well-known Doppler Effect) on the angle, with respect to the incoming proton beam, of gamma ray emission. Only those gammas with precisely the correct energy, i.e. the correct resonant absorption angle of about 80.66°±0.5°, can be resonantly absorbed. Non-resonant attenuation (scattering) can occur at any angle.

In view of the above, and as a central concept of the present invention, if the transmitted gamma ray flux through an object of interest is measured at the angle appropriate for resonant absorption and also measured at different angles from the resonant absorption angle, then the difference (with a small known angular correction to account for resonant gammas intersecting the object at a slightly different but known angles compared to the non-resonant gammas) between these two measurements is due to resonant absorption. Thus, and in contrast to the prior art, the present invention measures the transmitted gamma rays, and the attenuation caused by the object of interest, by comparing the measured intensity at a detector or detectors of the resonant transmitted gamma rays (transmitted through the object of interest) to the intensity measured at a detector or detectors which measure the intensity without resonant attenuation.

To make the required measurements, detectors are disposed which span beyond the resonant absorption angle. The detectors are also disposed so as to have a sufficient spatial resolution that allows the resonant absorption and non-resonant absorption transmission to be spatially (angularly sensitive) resolved. The difference between the resonant absorption and non-resonant absorption transmission yields the resonant absorption. Of course, the detectors outside of the resonant absorption angle of 80.66°±0.5° measure the transmission through the object with no resonant absorption or substantially no resonant absorption. From this data, the resonant absorption (attenuation) at about 80.66° can be closely estimated. Thus, while the transmission at about 80.66° is a result of both non-resonant absorption (attenuation) and resonant absorption (attenuation), the non-resonant absorption can be subtracted from that transmission, and the difference, which is the resonant absorption, is due to the nitrogen content in the object of interest.

As can be appreciated from the above, this technique is viable only if adequate spatial (angular) resolution is achieved by the detectors. As noted above, the correct angle for resonant absorption is in relation to the direction at which the proton beam hits the target. From this it will be further appreciated that if the proton beam has a rather large angular spread, this will be reflected in a likewise relatively large angular spread of gamma ray beams suitable for resonant absorption and, consequently, result in a decrease in the ultimate spatial resolution within the object of interest. Therefore, the larger the proton beam spot on the target, the poorer the spatial resolution at the detectors, because of the wider gamma ray beam which results. To achieve a proper proton beam spot, the design of the accelerator for the protons is, therefore, critical in achieving a desired limit on the proton beam divergency and beam size at the target.

Thus, very briefly stated, the present invention provides an apparatus for determining the amount of nitrogen in an object containing nitrogenous compounds. The method comprises supplying a support means for supporting the object. At least one gamma ray beam means is disposed on one side of the support for producing a beam of about 9.2 MeV gamma rays and in sufficient intensity to cause measurable resonant absorption by $^{14}N$ in the nitrogenous compounds.

Directing means are disposed between the gamma ray beam means and the support for directing the gamma ray beam to the support at predetermined angles thereto, including resonant absorption angles, such that the gamma ray beam forms a path which encounters at least a portion of the object when disposed on the support.

An array of gamma ray detectors are disposed on an opposite side of the support for detecting gamma rays of about 9.2 MeV transmitted through the object at both resonant and non-resonant angles.

A computation means is provided for computing the difference in the amount of transmitted gamma rays detected by the detectors at the resonant angles and the non-resonant angles, and wherein the difference is related to the amount of nitrogenous compounds in the object.

Likewise, there is provided a method for determining the amount of nitrogen in an object containing nitrogenous compounds by providing a support for supporting the object, generating at least one gamma ray beam with about 9.2 MeV gamma rays in sufficient intensity to cause measurable resonant absorption by the $^{14}N$ in the nitrogenous compounds, directing the at least one gamma ray beam to the support at a predetermined angle such that the at least one gamma ray beam will form a path which encounters at least a portion of the object disposed on the support, arraying a plurality of about 9.2 MeV gamma ray detectors on a side of the support opposite from the side thereof to which the at least one gamma ray beam is directed such that gamma ray beams transmitted through the object will impinge on the so-produced array of detectors at both resonant and non-resonant angles, and computing the difference in the amount of transmitted gamma rays received by the detectors at the resonant angle and the non-resonant angle, wherein that difference is related to the amount of nitrogenous compounds in the object.

DETAILED DESCRIPTION OF PREFERRED EMBODIMENTS OF THE INVENTION

Figure 1:
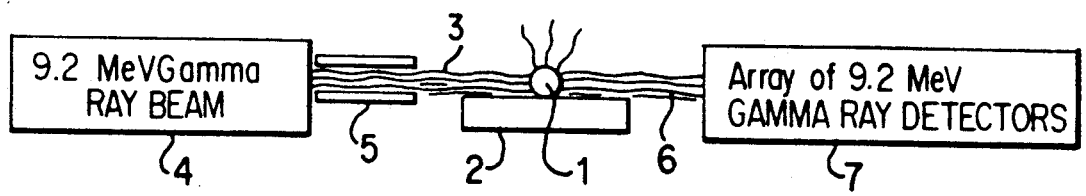
FIG. 1 is a diagrammatic view of the overall apparatus and process of the invention.

FIG. 1 shows, in highly diagrammatic form, the overall apparatus and method of the invention. Thus, an object 1 may contain nitrogenous compounds, as well as non-nitrogenous compounds. The non-nitrogenous compounds may be any compound which will not resonantly absorb the 9.2 MeV gamma ray beams. Thus, the non-nitrogenous compounds may contain elements such as oxygen, carbon, sulfur, hydrogen, etc. For example, that object may be any object containing both nitrogenous compounds and non-nitrogenous compounds, such as fertilizers, explosives, drugs, foods, and the like. Object 1 is supported on a support means 2, which support means is configured for the particular object 1. For example, if explosives in a container, e.g. a travel bag or luggage, are to be detected, then support 2 may be a conveyor or a more complex rotating-translation system. On the other hand, if the protein content of milk is to be determined, support 2 may be a pipe through which that milk flows. On the other hand, if the object is to be a grain or cereal for which the protein content is to be determined, the support 2 may be a chute or the like. In any event, the support 2 is configured for convenience of conveying the object 1 through the generated gamma ray beam 3 produced by the gamma ray beam means 4. In this latter regard, there is at least one gamma ray beam means 4 for generating, correspondingly, at least one gamma ray beam 3, and the gamma ray beam means 4 is disposed on one side of support 2. The gamma ray beam means 4 must not only produce a gamma ray beam of about 9.2 MeV gamma rays, but in sufficient intensity to cause measurable resonance absorption of $^{14}N$ in the nitrogenous compounds of the object 1.

A directing means 5 is disposed between the generating gamma ray beam means 4 and the support 2. The directing means 5 directs the generated gamma ray beam 3 to the support 2 in a predetermined angle or angles thereto, as explained more fully hereinafter in connection with FIG. 2. Whatever that angle, the angle is such that the generated gamma ray beam 3 forms a path which encounters at least a portion of object 1 disposed on support 2. In this regard, it may not be possible for the entire object to be intercepted by the gamma ray beam 3, for example, when the object is milk flowing in a pipe, grain passing through a chute, or even a large piece of luggage being examined for explosives. In other circumstances, however, the entire object may intercept beam 3, and the detection carried out in toto. The directing means 5 can be a conventional collimator for collimating the gamma ray beam.

In an analysis of luggage, e.g. for explosives or drugs, it is convenient to measure the transmission (attenuation) at many angles through the luggage and to compute both components of measured attenuation from subvolumes of the object as small as can be resolved by the detectors, prior to subtraction of the resonant and non-resonant transmissions, as explained above. The non-resonant attenuation provides an estimate of the total mass density of these subvolumes. The resonant absorption provides an estimate of the nitrogen density in these subvolumes. By knowing the total mass density of the subvolumes, and the nitrogen density of these subvolumes, the probability of explosives or drug detection is increased, since the characteristics of total mass density and nitrogen density in a subvolume can differentiate from other nitrogenous compounds such as certain plastics, e.g. melamine and polyurethane plastics. For example, when the total mass density of a subvolume, e.g. in grams per cubic centimeter, is about 1.2 to 2.5 and the nitrogen density is about 0.05 to 0.9, the detected nitrogenous material in the subvolume is very likely to be an explosive.

As noted above, the detectors measure the number of gamma rays transmitted through the object and, after the above-discussed computation, yield both the total amount of nitrogen and a quantity which is related to the total amount of mass between the gamma ray source and the detectors. By carrying out these measurements at a sufficient number of angles (gamma ray beam with respect to the object), it is possible, using known tomography algorithms, to compute the amount of total mass and the total nitrogen mass in these small volumes. The mass per volume (from non-resonant attenuation) and the nitrogen mass per volume (from resonant attenuation) are, therefore, useful in reducing the possibility of incorrectly identifying explosives and drugs. This is considerably different from the prior art which looks only for nitrogen and the results can be confused, since several well known substances, particularly plastics such as polyurethane plastics, have similar nitrogen densities to explosives. To make a reliable (high probability of detection and low false alarm rate) differentiation between explosives and the plastics, as well as other materials which might be in luggage, both of the masses, noted above, are determined.

To efficiently detect various shapes and objects, as explained above, gamma ray beams should traverse (illuminate) the object from multiple angles, and this can be achieved either by multiple beams or by rotating the object within the gamma ray beam, or by rotating the gamma ray beam itself. This latter can be achieved, for example, by moving the proton beam and target or a combination of these can be used. The number of angles (directions) at which transmission measurements should be made, depends on the spacial resolution required at the object. By measuring the transmission attenuation at many directions (angles) followed by computer-aided back projection in a known manner, the attenuation due to the small volumes where these various gamma ray beams intersect can be computed. The result is a three dimensional matrix made up of small volumes whose gamma ray attenuation is known.

When nitrogenous compounds are in object 1, the gamma rays are resonantly absorbed by the nitrogen of those nitrogenous compounds when at the above-noted resonant absorption angle. By disposing the detectors such as to span the resonant absorption angle and to span, usually, closely adjacent angles, and by using detectors of adequate spatial resolution, both resonant and non-resonant absorption transmission (or the inverse attenuation) can be detected by the detectors.

A computation means, e.g. a computer, 8 receives the output of the array 7 of gamma ray detectors, and the computation means computes the difference in the amount of gamma rays 6 received by the detectors in the array 7 at the resonant and non-resonant absorption transmission angles. That difference in detected gamma rays at these separate angles is related to the amount of nitrogenous compound(s) in the object, as discussed above.

The number of detectors and the array of the detectors is chosen for the particular object being examined. For example, a flat or nearly flat (or in the form of an arc) array of 10 to 100 detectors may be used when examining luggage, but a curved array of only 3 to 15 detectors may be used when examining flowing milk for protein content.

As noted above, an important aspect of the present invention is that of using detectors which give good spatial resolution, in terms of the angles of the transmitted gamma ray beams. This spatial resolution, of course, should be such that it can resolve the angular range in which resonant absorption occurs from those angles in which resonant absorption does not occur. However, and very importantly, this also means that there is no need to use nitrogen-loaded detectors, as required in the prior art, to determine gamma rays which are suitable for resonant absorption. Nitrogen-loaded detectors are very inefficient and have been a constant problem in the art. In the present invention, a wide range of detectors may be used. It is only necessary that the detectors be disposed such that their positions are capable of resolving not only the spatial angular differences between the non-resonant angles and the resonant angles of transmission, but also the small angles subtended by thin sheets of explosives.

It will also be appreciated that contrary to the prior art, the present invention does not measure the scattered gamma rays. This requires detectors capable of distinguishing resonant and non-resonant attenuation, and this is a very costly non-practical approach to the problem. In the present invention where the transmitted gamma rays are measured, the resonant attenuation by the object is determined by comparing the measured resonant plus non-resonant intensity of a detector to that of a detector which measures the intensity without resonant attenuation by virtue of their angular displacement, not by virtue of the design of the detector. It will be noted, however, that some minor attenuation is due to scattering. This is because many of the resonantly absorbed gammas result in the release of a proton of about 1.75 MeV through the inverse reaction at the target. However, scattered gammas are not part of the present invention, and this is a substantial distinction from the prior art.

Figure 2:
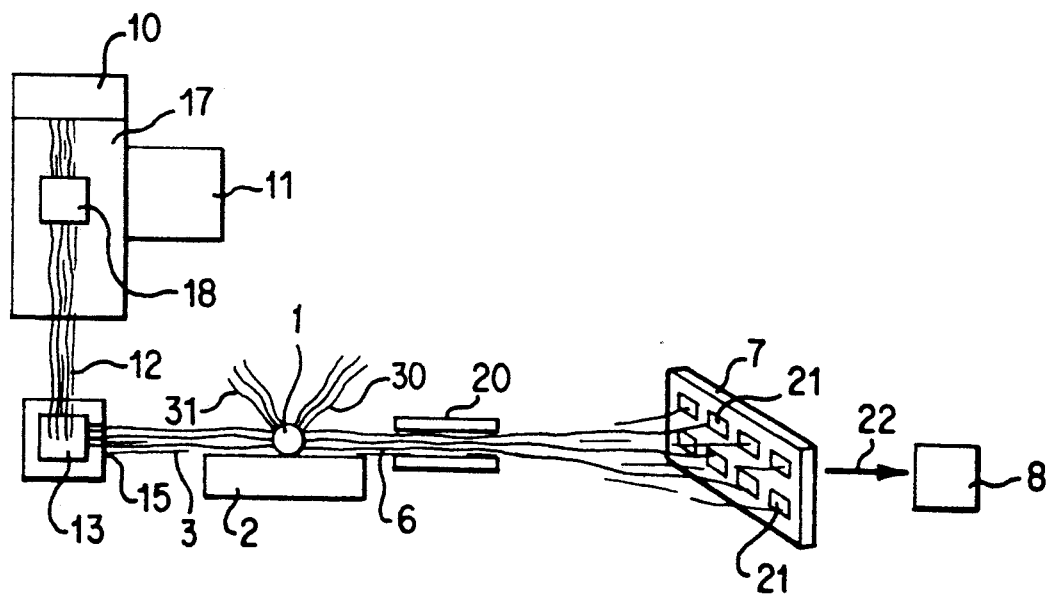
FIG. 2 is a schematic view of preferred apparatus for carrying out the method of the invention.

While FIG. 1 very briefly shows the overall arrangement of the apparatus and method of operation thereof, the invention will be further understood by the illustration in FIG. 2, which shows a preferred apparatus for carrying out the present invention. Parts of the apparatus which are similar to the parts of FIG. 1 have like reference numerals.

As shown in FIG. 2, the gamma ray beam 3 generated by gamma ray beam means 4 of Figure 1 is achieved by providing a hydrogen ion source 10 capable of producing about 5–20 mA of protons or negative hydrogen ions. The ion source 10 is coupled with a high voltage power supply 11 capable of accelerating the protons or ions to about 1.75 MeV to produce a proton beam of about 1.75 MeV. That about 1.75 MeV proton beam 12 impinges upon a gamma ray producing target material 13, e.g. $^{13}C$, capable of generating the about 9.2 MeV gamma ray beam 3 of the required high intensity.

In order to provide the required gamma ray beam of about 9.2 MeV, it is necessary that the proton beam 12 have a high energy stability, and, therefore, the high voltage power supply 11 should be capable of accelerating the protons within about 0.1% energy stability, and more preferably within about 0.01% energy stability. Otherwise, the necessary gamma ray beam will not be adequately produced, and the accuracy of the detection will deteriorate. Instead of the collimator used for the directing means 5 of FIG. 1, collimating slits 15 may be used. To measure the transmitted about 9.2 MeV gamma ray flux at the resonant angle and non-resonant angles, two sets of collimators may be used or the data can be obtained with the use of position sensitive detectors spanning the resonant angles. Also, conveniently, the ion source 10 may be operated in an accelerating column 17, as diagrammatically shown in FIG. 2, and the high voltage power supply 11 may be operated with such a column, again as shown diagrammatically in FIG. 2, for accelerating the protons. Also, an electron stripper 18 must be provided in the accelerating apparatus when negative hydrogen ions are used.

While a number of particle accelerators could be used to provide the above 1.75 MeV protons, it has been found that the so-called Tandem accelerator is far preferable for a number of reasons. In this device a negative hydrogen ion beam generated from ion source 10 (a proton with two electrons) is accelerated by the positive voltage of high voltage supply 11 to approximately one half the final energy. At this point, two electrons are removed by electron stripper 18 and the same voltage potential can then be used to accelerate through the same voltage back to ground which yields the required energy. One of the key elements of this approach is the stripper, where during the stripping process, Coulomb scattering causes the proton beam to have an unacceptably large divergence unless special precautions are followed. In the present invention, the beam is focused on a small spot with large divergence prior to stripping. The stripping then adds a negligible contribution to the already high beam divergence. Immediately after the stripping, the proton beam is focused to a nearly parallel beam with acceptable divergence. While such Tandem accelerators are known in the art, they are not known for present purposes.

As noted above, the target material 13 must produce the required gamma ray beam of about 9.2 MeV with the required intensity for causing resonance absorption by $^{14}N$ in the nitrogenous compounds. A number of such target materials are known to the art, and may be used, but preferably, $^{13}C$ is used, since this provides a very precise gamma ray beam of about 9.2 MeV with the required intensity, so long as the high energy proton beam, described above, strikes that target at the correct energy and within the required divergence.

The transmitted beam 6 may also be directed, if desired, by a directing device, such as a conventional collimator 20, and the transmitted beam 6 then strikes the array 7 of gamma ray detectors having a plurality of like gamma ray detectors 21. The gamma ray detectors 21 (and associated electronics which are known to the art) have specific sensitivities to substantially only 9.2 MeV gamma rays.

For certain applications, more than one gamma ray beam 3 may be used, e.g. the use of additional beams 30 and 31 may be used or one gamma ray beam at more than one angle. This is particularly useful when the nitrogenous compound is in a thin form, such as a thin sheet of explosive in a suitcase. With three beams, for example, at different angles, e.g. 90° from each other, at least one of those beams will strike the thin sheet in an oblique manner, thereby increasing the cross section for detection, and with the three beams used for a single detection, the accuracy of that detection can be very substantially increased, and obviate the difficulty in the prior art, as noted above. Each of the additional beams, e.g. beams 30 and 31, will be generated in the same manner as beam 3 and detected, as described above. A similar advantage is obtained by rotating the object through one or more beams.

Thus, when the object contains an explosive nitrogenous compound in sufficient quantities and the object is in a container, for example a travel bag, and the support means is configured to support the travel bag, e.g. the support means is a movable (translation and/or rotation) conveyor for supporting the travel bag, a plurality of gamma ray beams disposed at angles to each other can detect even thin sheets of explosive. However, with such a plurality of generated gamma ray beams, it is important that the angles between the various beams are sufficient so that the thin sheet of explosive nitrogenous compound is detected by the detectors. With appropriate angles, thin sheets of explosives of less than oneeighth inch may be detected, particularly when the angle between the beams is about 90° (or better yet at many angles) to each other.

On the other hand, where the object is a grain or milk product, for example, the support means is configured to support the grain or milk product, e.g. a chute or pipe or the like, and the support means is movable or the object is movable on the support means for moving the grain or milk product, e.g. a gravity chute for grain or a pump for pumping milk.

In each case, however, the detectors may be arrayed so as to determine the size, position or thickness of the object of interest. In the first above example, the array of detectors would be positioned so as to determine the size, position or thickness of an explosive nitrogenous compound in the travel bag, and in the second of the above examples, the detectors are arrayed such as to determine the amount of protein in the grain or milk product.

Figure 3:
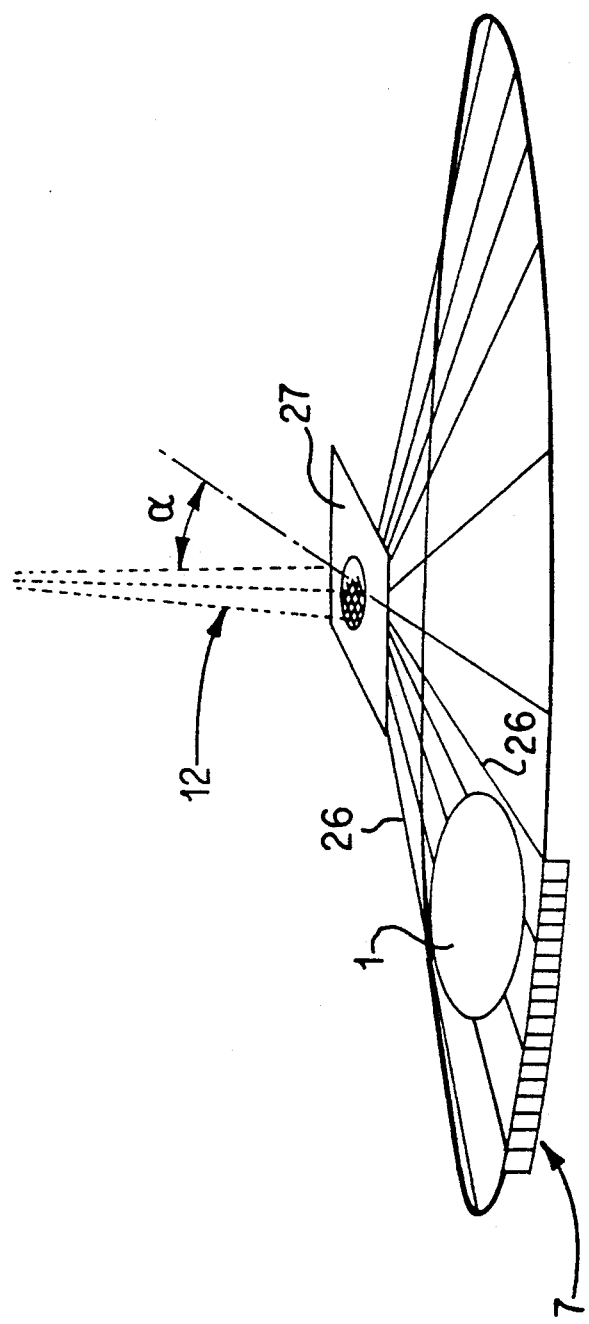
FIG. 3 is a schematic view of another embodiment of the apparatus.

As shown in FIG. 3, the object 1 (baggage) is between the array 7 of detectors and a gamma ray beam 26, somewhat in a cone shape. The proton beam 12 hits target 27. When the angle α is about 80.66°±0.5°, resonant absorption is possible. Collimators may also limit the angle to 80.66° plus or minus several degrees. Of course, in general, only a portion of the beam 26 is useful for detection purposes, and, therefore, the array 7 of detectors need only span that useful portion. However, the arc of the detectors should include all angles at which gamma rays have penetrated the object 1 and have been resonantly absorbed. In this regard, a rectangular array of position sensitive detectors may be used.

As can be appreciated from the above, an important feature of the present invention is in regard to the particular detectors, and the array of the detectors, used for detecting the nitrogenous compounds. As opposed to the prior art mentioned above, the present detectors are not nitrogen-rich detectors, but are detectors which can directly detect about 9.2 MeV gamma rays. They must be capable of good spatial resolution to separate the about 9.2 MeV gammas at the resonant angle from those gammas at non-resonant angles. Suitable detectors in this regard are specially shaped bismuth germanium oxide (BGO), sodium iodide (NI), wire chambers, etc. (See Rogers, Joel, IEEE Transactions on Nuclear Science, NS-39, pp. 1063-1068 (1992), for discussions of detectors and operations thereof, which disclosure is incorporated herein by reference.)

What is claimed is:

1. An apparatus for determining the amount of nitrogen in an object containing nitrogenous compounds, comprising:
   (1) a support means for supporting said object;
   (2) at least one gamma ray beam means disposed on one side of said support for producing a beam of about 9.2 MeV gamma rays and in sufficient intensity to cause measurable resonant absorption thereof by $^{14}$N in the nitrogenous compounds;
   (3) directing means disposed between the gamma ray beam means and the support for directing the gamma ray beam to said support at a predetermined angle thereto, such that the gamma ray beam forms a path which encounters at least a portion of the object when disposed on the support;
   (4) an array of gamma ray detectors disposed on an opposite side of the support for detecting gamma rays of about 9.2 MeV transmitted through said object at both resonant and non-resonant angles; and
   (5) computation means for computing the difference in the amount of transmitted gamma rays detected by the detectors at the resonant angles and non-resonant angles, wherein the difference is related to the amount of nitrogenous compounds in the object.

2. The apparatus of claim 1 wherein proton beam generating means generates about 1.75 MeV protons, which beam impinges upon a gamma ray producing target material capable of emitting said about 9.2 MeV gamma ray beam in high intensity.

3. The apparatus of claim 2 wherein the gamma rays emitted from the target include gamma rays at a resonant absorption angle of about 80.66°±0.5°.

4. The apparatus of claim 1 wherein the array of detectors span the resonant absorption angles and non-resonant absorption angles.

5. The apparatus of claim 3 wherein the disposition of the detectors is such that the resonant absorption transmission is resolvable from the non-resonant absorption transmission, whereby the detectors outside of the 80.66°±0.5° resonant absorption angle measure non-resonant absorption transmission with substantially no resonant absorption transmission.

6. The apparatus of claim 5 wherein the difference in non-resonant attenuation and resonant attenuation is due to the nitrogen content of the object.

7. The apparatus of claim 2 wherein an ion source capable of producing about 5 mA to about 20 mA of protons is coupled with a high voltage power supply capable of accelerating the protons to about 1.75 MeV to produce said proton beam.

8. The apparatus of claim 7 wherein the high voltage power supply is capable of accelerating said protons with about 0.1% energy stability.

9. The apparatus of claim 1 wherein the directing means include collimating slits.

10. The apparatus of claim 7 wherein the high voltage power supply is operably coupled with an acceleration column for accelerating the protons.

11. The apparatus of claim 10 wherein the ion source is a negative ion source and an electron stripper is disposed in the acceleration column.

12. The apparatus of claim 2 wherein the gamma ray producing target is $^{13}$C.

13. The apparatus of claim 1 wherein the object contains an explosive nitrogenous compound in sufficient quantity to cause an explosion, the object is in a container for the nitrogenous compound and said support means is configured to support said container.

14. The apparatus of claim 13 wherein the support is a movable conveyor for supporting, moving and/or rotating the container.

15. The apparatus of claim 14 wherein a plurality of gamma ray beams are disposed at angles to each other and wherein the angles are sufficient so that thin sheets of explosive nitrogenous compound are detectable by said detectors.

16. The apparatus of claim 15 wherein the angles are sufficient that a said thin sheet of less than ⅛ inch may be so detected.

17. The apparatus of claim 1 wherein only one gamma ray beam is provided and the object is rotated through said beam.

18. The apparatus of claim 13 wherein the detectors are arrayed such as to determine the size, position or thickness of the explosive nitrogenous compound in the container.

19. The apparatus of claim 1 wherein the object is a grain or milk product and said support means is configured to support said grain or milk product.

20. A method for determining the amount of nitrogen in an object containing nitrogenous compounds, comprising:
(1) providing a support for supporting said object;
(2) generating at least one gamma ray beam with about 9.2 MeV gamma rays in sufficient intensity to cause measurable resonance absorption thereof by $^{14}$N in the nitrogenous compounds;
(3) directing the at least one gamma ray beam to the support at a predetermined angle such that the at least one gamma ray beam will form a path which encounters at least a portion of said object when disposed on the support;
(4) arraying a plurality of about 9.2 MeV gamma ray detectors on a side of the support opposite from a side thereof to which the at least one gamma ray beam is directed such that a gamma ray beam transmitted through the object will impinge on the so-produced array of detectors at both resonant and non-resonant angles; and
(5) computing the difference in the amount of transmitted gamma rays received by the detectors at the resonant angles and non-resonant angles, and wherein said difference is related to the amount of the nitrogenous compounds in said object.

21. The method of claim 20 wherein about a 1.75 MeV proton beam is impinged on a gamma ray producing target material capable of generating said about 9.2 MeV gamma ray beam of high intensity.

22. The method of claim 21, wherein the gamma rays emitted from the target include gamma rays at a resonant absorption angle of about 80.66°±0.5°.

23. The method of claim 20 wherein the array of detectors span the resonant absorption angles and non-resonant absorption angles.

24. The method of claim 22 wherein the disposition of the detectors is such that the resonant absorption transmission is resolvable from the non-resonant absorption transmission, whereby the detectors outside of the 80.66°±0.5° resonant absorption angle measure non-resonant absorption transmission with substantially no resonant absorption transmission.

25. The method of claim 24 wherein the difference in non-resonant attenuation and resonant attenuation is due to the nitrogen content of the object.

26. The method of claim 21 wherein protons or negative hydrogen ions are generated from an ion source and accelerated with a high voltage power supply to produce said about 1.75 MeV proton beam.

27. The method of claim 20 wherein the at least one gamma ray beam is directed by passing the beam through collimating slits.

28. The method of claim 26 wherein the protons or negative hydrogen ions are passed through an acceleration column while being accelerated by said high voltage power supply.

29. The method of claim 28 wherein the ion source generates negative hydrogen ions and the ions are passed through an electron stripper in the acceleration column.

30. The method of claim 21 wherein said target material is $^{13}$C.

31. The method of claim 20 wherein the object contains an explosive nitrogenous compound in sufficient quantity to cause an explosion, the object is a container for the nitrogenous compound and the said beam is directed in a path to at least partially traverse a portion of the container.

32. The method of claim 31 wherein the support is a conveyor and the container is moved along the conveyor and through the said beam.

33. The method of claim 32 wherein a plurality of gamma ray beams are disposed at angles to each other and wherein the angles are sufficient that thin sheets of the explosive nitrogenous compound in the container are detectable by said detector.

34. The method of claim 32 wherein the container is rotated through said beam.

35. The method of claim 31 wherein the detectors are arrayed such as to determine the size, position or thickness of the explosive nitrogenous compound in the container.

36. The method of claim 20 wherein the object is a grain or milk product, and said beam is directed in a path to at least partially traverse a portion of the grain or milk product.

37. The method of claim 31 wherein the container is a travel bag.

38. The method of claim 31 wherein said beam is rotated about the container.

39. The method of claim 38 wherein the detectors are rotated about the container.

40. The method of claim 31 wherein the container is moved through said beam a plurality of times in a plurality of different orientations to said beam.

* * * * *